United States Patent [19]

White

[11] 4,049,121

[45] Sept. 20, 1977

[54] MOISTURE DETECTION SYSTEM FOR A STERILE PACKAGE

[75] Inventor: Leonard Alan White, Gurnee, Ill.

[73] Assignee: Baxter Travenol Laboratories, Inc., Deerfield, Ill.

[21] Appl. No.: 705,212

[22] Filed: July 14, 1976

[51] Int. Cl.² .................. A61B 19/02; B65P 77/22; G01D 13/00; A22C 17/10

[52] U.S. Cl. .................. 206/439; 206/459; 116/DIG. 7; 116/114 AB; 116/118 A; 426/87

[58] Field of Search .................. 206/459, 439; 116/114 AB, 118 A, DIG. 7; 426/87, 88, 383

[56] References Cited

U.S. PATENT DOCUMENTS

| | | | |
|---|---|---|---|
| 3,093,242 | 6/1963 | Huyck et al. | 206/459 |
| 3,263,892 | 8/1966 | Danyi et al. | 206/459 |
| 3,533,548 | 10/1970 | Taterka | 206/459 |
| 3,786,777 | 1/1974 | Smith et al. | 116/114 AB |
| 3,844,718 | 10/1974 | Cohen | 426/88 |

*Primary Examiner*—William Price
*Assistant Examiner*—Douglas B. Farrow
*Attorney, Agent, or Firm*—George H. Gerstman; Paul C. Flattery; John P. Kirby, Jr.

[57] ABSTRACT

A system for indicating the presence of water in a sterile package is shown in the illustrative arrangement by the use of a water soluble pattern of ink or dye behind a gas permeable barrier provided to such package to enable sterilization of the package contents. The pattern is printed either on the paper of the barrier or on the sealing coating provided on the barrier paper for attachment to the package shell or it is printed on a separate member deposited in the package.

17 Claims, 5 Drawing Figures

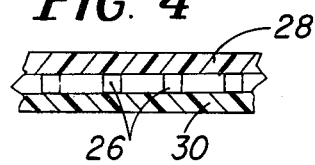
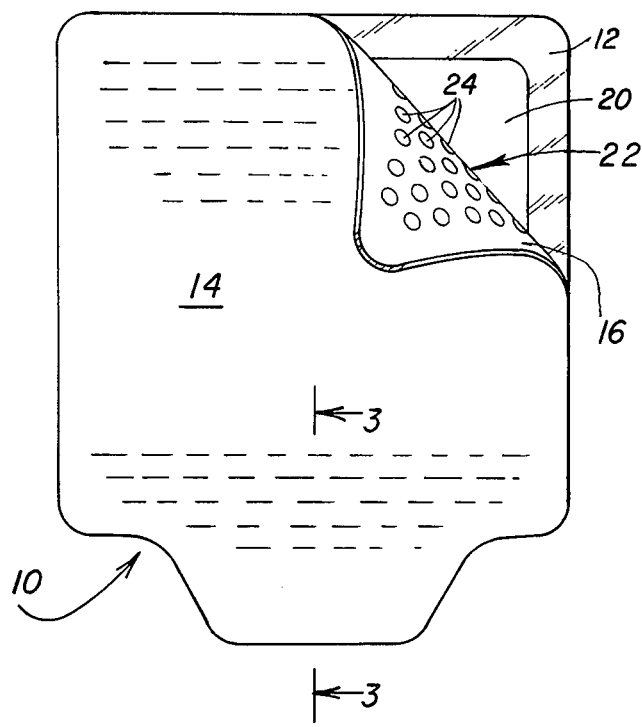
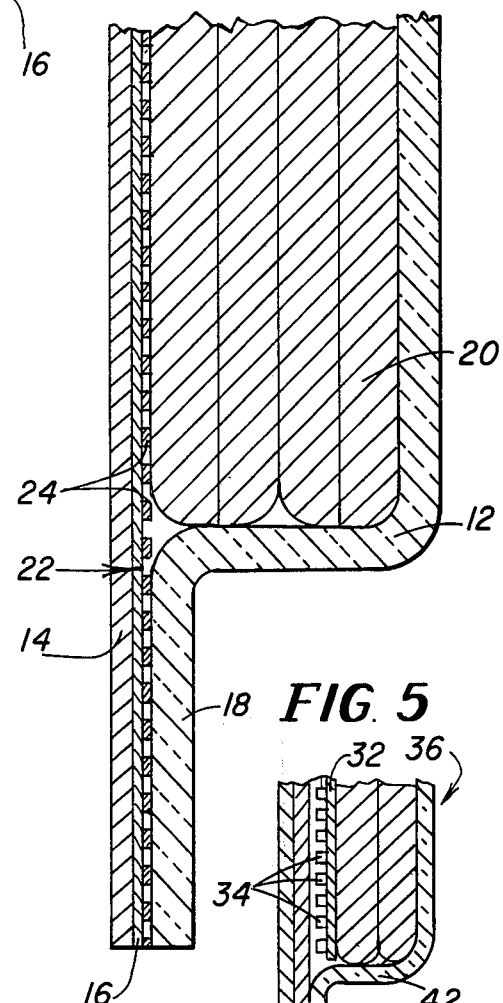
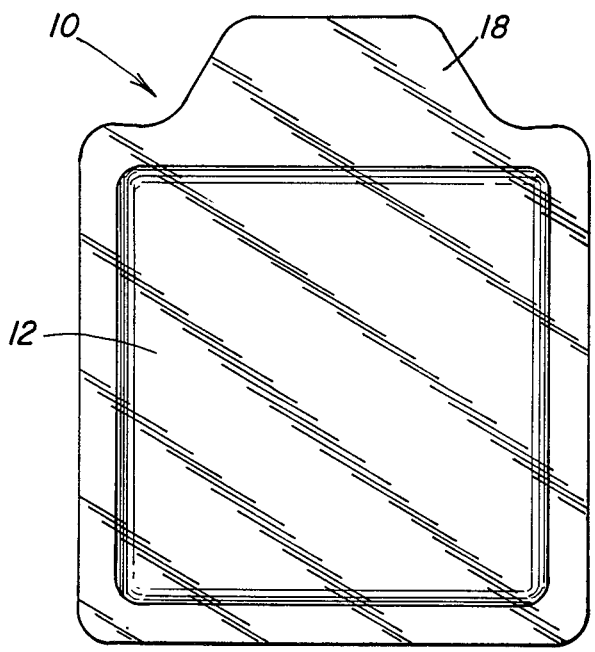
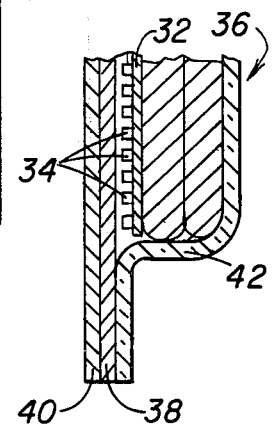

MOISTURE DETECTION SYSTEM FOR A STERILE PACKAGE

BACKGROUND OF THE INVENTION

This invention relates in general to a sterile package water detection system.

Sterile packages, such as blister packages or surgical kits, generally include a plastic shell having a barrier lid sealed thereto by means of a heat sealable coating on the reverse side of the lid. The package contents and interior are sterilized by passing a gas, such as ethylene oxide, through the pores of the lid and its coating. The pores are small enough to resist bacterial penetration, but may pass moisture. If even a small quantity of water should pass the barrier lid, the sterile condition may be lost.

One problem therefore is to provide an indication that water penetration has occurred.

Another problem is that after a package has been penetrated by water and dried, a memory or record of the prior wetting must be retained to indicate the possible contamination. Still another problem is that such moisture indicating system must be economical and compatible with presently used materials and practices.

Prior art moisture or water indicators using color-change compositions are sometimes ineffective because the operator must be aware of what color designates a moisture condition. Also, the color change may be subtle and not easily differentiated. Further, the operator might be color blind to the color change. Additionally, most moisture or water detection papers do not leave a permanent record. For example, commonly used cobalt chloride detection paper will turn from blue (dry condition) to pink (wet condition). However, upon subsequent drying the paper will return to blue without leaving a record of being wetted.

Accordingly, one object of the present invention is to provide a novel water detection system for a sterile package.

Another object of the present invention is to provide a water detection system for a sterile package which indicates the leak occurrence, after the water has dried.

Still another object of the present invention is to provide a water detection system for a sterile package which is economical and which would readily and immediately indicate a moisture condition.

Other objects and advantages of the invention will become apparent as the description proceeds.

SUMMARY OF THE INVENTION

The present invention provides a water detection system for a sterile package by incorporating a water altered pattern in the package behind the barrier lid or on the outside of the barrier lid. The change in appearance in the pattern on contact with a small amount of water provides a permanent record that water has permeated the package.

In the illustrative embodiments, the pattern is provided by printing either the back of the barrier lid or the heat sealable coating thereon with a water soluble pattern of ink or fluorescent dye, which smears or smudges to cover a relatively large area on contact with a small amount of water. Alternatively, a separate material bearing the dye is deposited in the package, but in any event an image indicating the water contamination is provided which is visible through the barrier and through the plastic shell, if transparent, or is visible when the lid is removed from the package.

The pattern is usually formed upon the rear surface of the barrier lid heat sealable coating in a matrix or grid, if a water based heat sealable coating is used, or the pattern is printed directly on the rear surface of the barrier lid if a non-aqueous heat sealable coating is used so that the coating may then be deposited on the printed pattern.

A more detailed explanation of the invention is provided in the following description and claims and is illustrated with accompanying drawings.

BRIEF DESCRIPTION OF THE DRAWINGS

FIG. 1 is a front elevational view of a sterile blister package employing the principles of the present invention with a portion of the barrier lid and heat sealable coating peeled away to reveal the pattern greatly enlarged;

FIG. 2 is a rear elevational view of the blister package shown in FIG. 1;

FIG. 3 is a sectional view of the blister package seen in FIG. 1 taken generally along the line 3—3 in FIG. 1 and showing the pattern and heat sealable coating in relatively greatly enlarged cross-section;

FIG. 4 is a fragmentary sectional view illustrating the pattern deposited directly on the rear surface of a barrier lid with the relative cross-section of the pattern and coating greatly enlarged; and FIG. 5 is a fragmentary sectional view illustrating a paper material bearing the pattern deposited in a sterile blister package.

DETAILED DESCRIPTION OF THE INVENTION

In FIGS. 1 and 2, a sterile blister package is indicated by the reference character 10. The package 10 includes a transparent plastic shell 12 which may be cup-shaped, box-shaped or have various other shapes, and a barrier lid 14 having a heat sealable coating 16 on the rear surface thereof.

A peripheral flange 18 on the open end of the shell 12 is sealed to lid 14 by means of the heat sealable coating 16, as best seen in FIG. 3, for sealing the contents 20, such as a gauze or packing or any other type of medical device or equipment, in the package 10. The coating 16 is deposited on the rear surface of lid 14 prior to its assembly to the shell 12 and the front surface is printed both with identification of the contents, etc., and a notice to observe the indicia of contamination to be described.

The lid 14 is normally of a paper stock material, such as a 60# surgical kraft paper or a non-woven material made from polyethylene fibers commonly sold under the trademark TYVEK by DuPont. The lid 14, together with the heat sealable coating 16, are permeable to a sterilizing gas, such as ethylene oxide, which sterilizes the contents and interior of the package. The "labyrinth" or "depth" filter formed by lid 14 will not normally pass particles over 0.22 microns, which is smaller than any known bacteria, but does admit moisture (although the coating will retard penetration). The contents 20 of the package can therefore become contaminated.

To indicate water contamination, a pattern 22 of dots 24 formed of a water soluble alcohol, acetone or other water compatible based ink, dye or fluorescent ink or dye is printed on the rear surface of the heat sealable coating, as shown greatly enlarged in FIGS. 1 and 3 wherein the cross-sectional area and size of the dots are shown greatly exaggerated. An example of a type of water soluble dye that may be used is sold by Ink Specialties Company, Arlington Heights, Illinois. The coating 16 extends between the dots on heat sealing.

The pattern is printed on the rear surface of the coating 16 in the form of a matrix of rows and columns of magenta or other color dots, as shown in FIG. 1, with adjacent rows and columns offset or in a grid. As a specific example, although no limitation is intended, a dot pattern with 1/32 inch diameter dots spaced 3/64 inches between centers has been found to be satisfactory. Penetration by water such as a single drop from a fine needle causes the ink or dye to bleed between the dots or through the lid and creates a smudge that is clearly visible on or through the lid 14, or on the underside of a peeled-off lid, or through portions of the transparent shell 12 not blocked by the contents.

As shown in FIG. 4, a pattern 26 of dots or a grid may be printed directly on the paper barrier lid 28, for example, and the pattern 26 covered by a heat sealable coating 30, which flows between the dots to make direct contact with the rear surface of the lid 28. However, it has been found that when the pattern is printed directly on the paper barrier lid 28 (under the coating 30), the lid may become extremely sensitive to moisture applied to the outside thereof. Such extreme sensitivity may be excessive for the purposes desired. For example, a lid having the pattern printed directly thereon in accordance with the FIG. 4 embodiment may demonstrate bleeding of the dot pattern when handled by a person with slightly damp hands, although there is actually no water contamination inside the package. For this reason, the FIG. 3 embodiment is generally preferred.

Alternatively, a sheet of paper 32 or the like, or paper-like material, carrying a pattern 34 of water soluble colored material (as shown in FIG. 5) may simply be deposited in the package or container 36 between the coating 38 on the rear surface of the barrier lid 40 and the plastic shell 42.

It is understood that various modifications and substitutions may be made by those skilled in the art without departing from the novel spirit and scope of the invention.

What we claim is:

1. A system for detecting water contamination which comprises: a package having sterile unfrozen contents covered by a gas permeable barrier; a water soluble dye pattern in said package, said pattern adapted to bleed in response to water in said package, for visibly indicating said water contamination.

2. The improvement described in claim 1, wherein said gas permeable barrier has a heat sealable coating on one side and wherein said water soluble dye pattern is printed on said heat sealable coating.

3. The improvement described in claim 1, wherein said gas permeable barrier is a non-woven material and said water soluble dye pattern is printed thereon and covered by said heat sealable coating.

4. The improvement described in claim 3, wherein said non-woven material is a paper stock.

5. The improvement described in claim 1, in which said dye pattern comprises a matrix of spaced dots in the form of a grid.

6. The improvement described in claim 1, in which said water soluble dye pattern is printed on a sheet for deposit in said package.

7. A sterile package including a gas permeable barrier having a heat sealable coating on one side, a plastic shell secured to said barrier adjacent said one side for enclosing the contents of said package, the improvement comprising a water soluble pattern in said package adapted to bleed in response to water contamination in the package.

8. The improvement described in claim 7, in which said pattern is formed from a fluorescent dye.

9. The improvement described in claim 7, in which said pattern is formed from a water compatible ink.

10. The improvement described in claim 7, wherein said pattern is printed on said heat sealable coating.

11. The improvement described in claim 7, wherein said gas permeable barrier is a non-woven material and said pattern is applied thereto and covered by said heat sealable coating.

12. The improvement described in claim 11, wherein said non-woven material is a paper stock.

13. The improvement described in claim 11, wherein said non-woven material is TYVEK material and said water compatible ink is alcohol based.

14. The improvement claimed in claim 11, wherein said heat sealable coating is a non-aqueous based coating.

15. The improvement described in claim 7, in which said pattern comprises a matrix of dots in the form of a grid.

16. The improvement described in claim 7, in which said pattern is printed on a sheet for deposit in said package.

17. A sterile package, which comprises: a lid formed of TYVEK material having a heat sealable coating on one side thereof; a plastic shell secured to said lid on said one side for enclosing the contents of said package; a water soluble dye pattern printed on said heat sealable coating and adapted to bleed in response to water in the package, said dye pattern comprising a matrix of dots in the form of a grid.

* * * * *